United States Patent
Lupo, Jr. et al.

[11] Patent Number: 6,110,888
[45] Date of Patent: Aug. 29, 2000

[54] SUBSTITUTED PHENOLS AS FRAGRANCE, FLAVOR AND ANTIMICROBIAL COMPOUNDS

[75] Inventors: Andrew T. Lupo, Jr., Emerson, N.J.; Tetsuo Nakatsu, Chappaqua, N.Y.; John Caldwell, Hewitt, N.J.; Raphael K. L. Kang, Northvale, N.J.; Alba T. Cilia, River Edge, N.J.; Augustinus G. Van Loveren, Bedford, N.Y.; Lolita Villamaria, Teaneck, N.J.

[73] Assignees: Takasago International Corporation, Japan; Takasago Institute for Interdisciplinary Science, Inc., Rockleigh, N.J.

[21] Appl. No.: 09/309,251

[22] Filed: May 10, 1999

[51] Int. Cl.$^7$ .............. A61K 7/46; A61K 7/00; A61K 7/16; A61K 7/32; A61K 7/06
[52] U.S. Cl. ............ 512/1; 424/49; 424/65; 424/70.1; 424/401; 424/405; 510/119; 510/130; 510/218; 510/276; 512/20; 512/25
[58] Field of Search .................... 424/401, 405, 424/49, 65, 70.1; 512/1, 20, 25; 510/119, 130, 218, 276

[56] References Cited

U.S. PATENT DOCUMENTS 4,689,175  8/1987  Broekhof .................. 512/20
5,800,803  9/1998  Mirajkar et al. .......... 424/54

*Primary Examiner*—Shelley A. Dodson
*Assistant Examiner*—Marina Lamm
*Attorney, Agent, or Firm*—Morrison Law Firm

[57] ABSTRACT

A fragrance and/or flavor compound of the general formula (I):

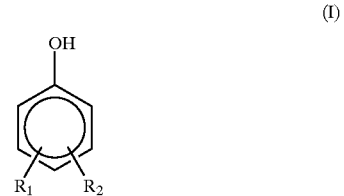

(I)

wherein $R_1$ is one of propyl or a 2-propenyl group and $R_2$ is a $C_1$–$C_5$ alkyl group, said compound having exactly one $R_1$ and from one to four $R_2$. The compounds possess antimicrobial activity as well as flavor or odor characteristics acceptable for use in flavors and fragrances, respectively. The compounds are useful in forming flavor and/or fragrance compositions having antimicrobial activity. Product formulations, such as detergents, are useful for imparting both acceptable fragrance and antimicrobial properties. Other product formulations, such as mouthwashes, are useful for imparting both acceptable flavor and antimicrobial properties.

33 Claims, No Drawings

SUBSTITUTED PHENOLS AS FRAGRANCE, FLAVOR AND ANTIMICROBIAL COMPOUNDS

BACKGROUND OF THE INVENTION

The present invention relates to substituted phenol compounds having antimicrobial activity. These compounds are useful as fragrance or flavor compounds having antimicrobial activity. The present invention further relates to detergent, personal care and other products having antimicrobial activity containing the substituted phenol compounds of the present invention.

Fragrances are commonly incorporated in a wide variety of household, personal care, and industrial items, from perfumes to cleansers, to impart a pleasing odor to the item. Some fragrances have been reported to have weak bacteriostatic activity. However, this activity is believed to be too weak to be of practical use. See J. A. Morris et al., J. Amer. Oil Chem. Soc. 56(5):595–603 (1979).

One way used to achieve sufficient antimicrobial activity of certain fragrances is to increase the effective fragrance ingredient concentration until the desired activity is achieved. For example, U.S. Pat. No. 5,306,707 used 30% effective perfume ingredients to achieve activity in the combination. However, this produces an active perfume having an odor that is not pleasing and is not acceptable to the consumer in a final consumer product. Further, these fragrances also have an unacceptably high odor intensity index as the perfumer tries to mask the odor of the effective material with large amounts of other fragrance ingredients or materials having a high intensity. There is an inverse relationship between the activity of the effective fragrance material and its odor acceptability; that is, as antimicrobial activity increases, odor acceptability decreases.

Certain precursors of the present invention have been shown to have antimicrobial activity. The compounds thymol, carvacrol, cinnamaldehyde and eugenol were tested alone or in combination against oral bacteria. The compounds showed an inhibitory activity on several microorganisms and a synergistic effect was observed with certain combinations. The four compounds can be used alone or in combination, such as eugenol and thymol, eugenol and carvacrol, thymol and carvacrol in the treatment of oral infectious diseases. See N. Didry et al., Pharm. Acta Helv., 69(1):25–8 (1994).

The antimicrobial activity of thymol, carvacrol, and cinnamaldehyde was also tested in several in vitro methods on bacteria involved in upper respiratory tract infections. The broad spectrum activity and synergistic effects observed with some combinations (especially thymol and carvacrol) could allow the use of the 3 compounds alone or in combination for the treatment of respiratory infections. N. Didry et al., Pharmazie, 48(4), 301–4 (1993). Although thymol and carvacrol have antimicrobial activity, use of these compounds is limited as flavors and fragrances due to their becoming hedonically unacceptable above certain concentrations.

Some of the compounds of the present invention have not been previously reported. Others have been reported for use as intermediates in synthesis reactions. These include ortho allyl thymol, ortho propyl thymol, para propyl carvacrol, ortho propyl carvacrol, para propyl thymol, ortho allyl para tert-butyl phenol, and ortho propyl para tert-butyl phenol. See Bu-Hou et al. "Bull. Soc. Chim. Fr.," vol. 5 p. 12 (1954); P. Sen, "J. Indian Chem. Soc.," vol. 30 p. 801 (1953); Rosenmund et al. "Arch. Pharm. (Weinheim Ger.)," vol 408 (1928); P. Sen "J. Indian Chem. Soc.," vol. 30, p. 61 (1953); and Rosenmund et al. "Arch. Pharm. (Weinheim Ger.)" vol. 313 (1927), respectively.

The present invention has also been determined to be suitable for flavor applications. The present invention used in certain combinations can have beneficial taste characteristics such as vanillin-like, spicy or herbal.

OBJECTS AND SUMMARY OF THE INVENTION

In light of the above, it is an object of the present invention to overcome the limitations of the prior art.

It is another object of the present invention to provide novel compounds useful as flavors and fragrances.

It is another object of the present invention to provide a fragrance composition which is both acceptable to consumers and exhibits antimicrobial activity.

It is another object of the present invention to provide a general purpose cleanser composition containing a fragrance which is both acceptable to consumers and exhibits antimicrobial activity.

It is another object of the present invention to provide various products having desirable fragrance and antimicrobial activity including soaps, fabric softeners, skin care products, disinfectants, sanitizers and related products.

It is another object of the present invention to provide a flavor composition which is both acceptable to consumers and exhibits antimicrobial activity.

It is another object of the present invention to provide various products having desirable flavor and antimicrobial activity including mouth washes, toothpastes, cough drops, nebulizers, inhalants and other related products.

We have discovered a way to create fragrances and flavors with sufficient antimicrobial activity to be useful and yet have a good odor and taste acceptability.

Briefly stated, the present invention is a fragrance or flavor compound having antimicrobial activity. The fragrance or flavor compound is described by the general formula (I):

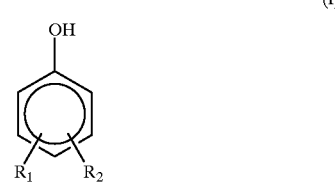

(I)

wherein $R_1$ is one of propyl or a 2-propenyl group and $R_2$ is a $C_1$–$C_5$ alkyl group, the compound having exactly one $R_1$ and from one to four $R_2$. The compound possesses antimicrobial activity as well as flavor and odor characteristics acceptable for use in flavors and fragrances. The compound can be used as a flavor or fragrance having antimicrobial activity as well as in flavor or fragrance formulations to be used in a variety of products.

The term "$C_1$ to $C_5$ alkyl" is defined to include straight or branched, saturated or unsaturated, carbon chains having from 1 to 5 carbon atoms. Examples of a $C_1$ to $C_5$ alkyl groups include methyl, ethyl, allyl, propyl, iso-propyl, butyl, iso-butyl, tert-butyl, and pentyl.

According to an embodiment of the present invention, a fragrance composition having antimicrobial activity is provided including a substituted phenol of the present invention in combination with a suitable carrier.

According to another embodiment of the present invention, a general purpose cleanser having antimicrobial activity is provided including about 0.25% of a substituted phenol fragrance of the present invention in combination with a suitable carrier and other adjunct ingredients.

According to an embodiment of the present invention, a flavor composition having antimicrobial activity is provided including a substituted phenol of the present invention in combination with a suitable carrier.

According to another embodiment of the present invention, a mouthwash having antimicrobial activity is provided including a suitable amount of a substituted phenol flavor of the present invention in combination with a suitable carrier and other adjunct ingredients.

The above, and other objects, features and advantages of the present invention will become apparent from the following description.

DETAILED DESCRIPTION OF THE PREFERRED EMBODIMENTS

As noted above, the present invention is directed to novel fragrance or flavor and antimicrobial compounds of the formula (I):

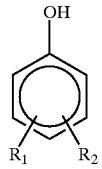

(I)

In the above formula (I), $R_1$ is one of propyl or a 2-propenyl group and $R_2$ is a $C_1$–$C_5$ alkyl group, the compound having exactly one $R_1$ and from one to four $R_2$.

For reasons of their fragrance or flavor characteristics, formulation benefits or antimicrobial activity, the compound of formula (I), wherein the hydroxyl group and $R_1$ are in a 1,2 or 1,4 substitution relationship are preferred classes of compounds within the scope of formula (I).

Specific compounds of formula (I) which are most preferred, for reasons of fragrance or flavor characteristics, formulation benefits and/or other values are as follows: ortho allyl thymol, para allyl thymol, ortho propyl thymol, para propyl thymol, ortho allyl carvacrol, para allyl carvacrol, ortho propyl carvacrol, para propyl carvacrol, ortho allyl para tert-butyl phenol, and ortho propyl para tert-butyl phenol.

The novel substituted phenol compounds of the present invention may be prepared in various fashions. In the preferable protocols, either thymol, carvacrol, or para tert-butyl phenol are used as a starting material. The invention is further described in the following Examples 1–4, and Embodiments 1–6, which are prophetic examples illustrating methods of preparation of the present invention.

Example 1 describes the preparation of ortho and para allyl thymol, a compound of the formula (1), wherein $R_1$ is a 2-propenyl group and one $R_2$ is a methyl group and another $R_2$ is an isopropyl group.

Example 2 describes the preparation of ortho and para allyl carvacrol, a compound of the formula (I), wherein $R_1$ is a 2-propenyl group and one $R_2$ is a methyl group and another $R_2$ is an isopropyl group.

Example 3 describes the preparation of ortho and para propyl thymol, a compound of the formula (I), wherein $R_1$ is a propyl group and one $R_2$ is a methyl group and another $R_2$ is an isopropyl group.

Example 4 describes the preparation of ortho and para propyl carvacrol, a compound of the formula (I), wherein $R_1$ is a propyl group and one $R_2$ is a methyl group and another $R_2$ is an isopropyl group.

Example 5 describes the preparation of ortho allyl para tert-butyl phenol, a compound of the formula (I), wherein $R_1$ is a 2-propenyl group and $R_2$ is a tert-butyl group.

Example 6 describes the preparation of ortho propyl para tert-butyl phenol, a compound of the formula (I), wherein $R_1$ is a propyl group and $R_2$ is a tert-butyl group.

Embodiment 1 describes a fragrance formulation using a compound of the formula (I).

Embodiment 2 describes a flavor formulation using a compound of the formula (I).

Embodiment 3 describes an antimicrobial fragrance formulation using a compound of the formula (I).

Embodiment 4 describes an antimicrobial flavor formulation using a compound of the formula (I).

Embodiment 5 describes a cleanser using a compound of the formula (I).

Embodiment 6 describes a mouthwash using a compound of the formula (I).

Preparation of the examples involves use of the starting materials of allyl thymol ether, allyl carvacrol ether, or allyl para tert-butyl phenyl ether prepared according to the following methods.

Allyl Thymol Ether

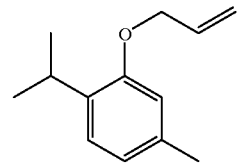

To a solution of thymol (45.1 g, 300 mmole) and acetone (250 ml) was added a mixture of solid potassium carbonate (45.6 g, 330 mmole) and potassium iodide (5.5 g, 33 mmole). The mixture was stirred and heated to reflux for 24 hours. The cooled reaction was concentrated via rotary evaporation and to the residue was added diethyl ether (200 ml). The mixture was washed with water (2×100 ml) and saturated aqueous NaCl solution (1×100 ml). The organic layer was dried over $Na_2SO_4$, filtered and evaporated to give the crude product. The crude product was distilled under vacuum (76–78° C. @ 0.8 mm Hg) to afford a colorless oil (52.0 g, 91%).

MS: $M^+$=190; $^1$H NMR (CDCl$_3$, 500 MHz) δ 1.21 (6H, d), 2.27 (3H, s), 3.31 (1H, m), 4.53 (2H, m), 5.25 (1H, dd), 5.42 (1H, dd), 6.07 (1H, m), 6.65 (1H, s), 6.75 (1H, dd),7.09 (1H, dd); $^{13}$C NMR (125 MHz, CDCl$_3$) 21.4, 22.8, 26.7, 68.9, 112.8, 116.7, 121.4, 126.0, 133.9, 134.2, 136.3, 155.8 ppm.

Allyl Carvacrol Ether

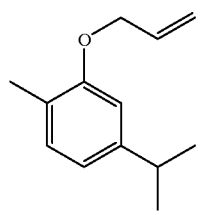

This material was prepared as described for allyl thymol ether except using carvacrol as a starting material. From carvacrol (45.1 g, 300 mmole) was obtained allyl carvacrol ether (51.0 g, 90%, 80–82° C. @ 0.8 mm Hg).

MS: $M^+$=190; $^1$H NMR (CDCl$_3$, 500 MHz) δ 1.24 (6H, d), 2.21 (3H, s), 2.86 (1H, m) 4.55 (2H, m), 5.28 (1H, dd), 5.46 (1H, dd), 6.07 (1H, m), 6.70 (1H, s), 6.73 (1H, dd), 7.06 (1H, d); $^{13}$C NMR (125 MHz, CDCl$_3$) 15.9, 24.2, 34.2, 68.9, 110.0, 116.8, 118.3, 124.4, 130.5, 133.9, 147.9, 156.8 ppm.

Allyl Para tert-Butyl Phenyl Ether

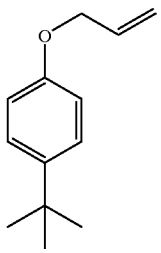

This material was prepared as described for allyl thymol ether except using para tert-butyl phenol as a starting material. From para tert-butyl phenol (100 g, 667 mmole) was obtained allyl para tert-butyl phenyl ether (105.0 g, 83%, 87° C. @ 2 mm Hg).

MS: M$^+$=190; $^1$H NMR (CDCl$_3$, 500 MHz): δ 1.30 (9H, s), 4.52 (2H, d), 5.27 (1H, d), 5.42 (1H, d), 6.05 (1H, m), 6.86 (2H, d), 7.30 (2H, d); $^{13}$C NMR (CDCl$_3$, 125 MHz): 31.6, 34.1, 68.9, 114.3, 117.5, 126.3, 133.7, 143.6, 156.4 ppm.

EXAMPLES 1a AND 1b

Ortho and Para Allyl Thymol:

A flask containing allyl thymol ether (50.0 g, 263 mmole) was heated under N$_2$ atmosphere at 200° C. for 4 hours. The mixture was cooled and purified via vacuum distillation (74–75° C. @ 0.7 mm Hg) to afford a colorless oil (49.0 g, 98%) consisting of ortho and para isomers (ortho:para=24:1 by GC). If desired, the isomers can be separated via silica gel column chromatography (10% ethyl ether in hexane) to provide ortho allyl thymol (1a) and para allyl thymol (1b).

Ortho Allyl Thymol (1a):

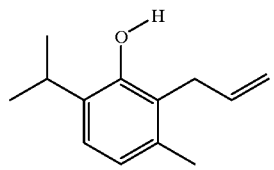

MS: M$^+$=190; $^1$H NMR (CDCl$_3$, 500 MHz) δ 1.25 (6H, dd), 2.27 (3H, s), 3.16 (1H, m), 3.44 (2H, m), 4.95 (1H, s), 5.12 (2H, t), 5.97 (1H, m), 6.77 (1H, d), 7.01 (1H, d); $^{13}$C NMR (125 MHz, CDCl$_3$) 19.6, 22.8, 27.1, 31.3, 116.0, 122.5, 123.3, 123.9, 132.4, 134.9, 135.7, 151.6 ppm.

Para Allyl Thymol (1b):

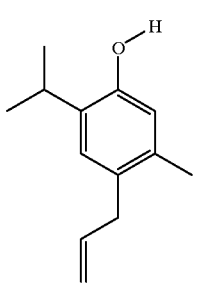

MS: M$^+$=190; $^1$H NMR (CDCl$_3$, 500 MHz) δ 1.23 (6H, dd), 2.2 (3H, s), 3.14 (1H, m), 3.29 (2H, m), 4.53 (1H, s), 5.02 (2H, t), 5.92 (1H, m), 6.56 (1H, s), 6.94 (1H, s); $^{13}$C NMR (125 MHz, CDCl$_3$) 18.9, 22.8, 27.0, 37.2, 115.2, 117.2, 121.7, 127.4, 130.4, 134.8, 137.3, 151.6 ppm.

EXAMPLES 2a AND 2b

Ortho and Para Allyl Carvacrol:

These materials were prepared as described in Example 1. From allyl carvacrol ether (50.0 g, 263 mmole) was obtained a colorless oil (48.3 g, 97%, 79° C. @ 0.7 mm Hg) consisting of ortho and para isomers (ortho:para=9:1 by GC). If desired, the isomers can be separated via silica gel column chromatography (10% ethyl ether in hexane) to provide ortho allyl carvacrol (2a) and para allyl carvacrol (2b).

Ortho Allyl Carvacrol (2a):

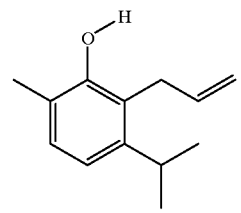

MS: M$^+$=190; $^1$H NMR (CDCl$_3$, 500 MHz) δ 1.19 (6H, d), 2.2 (3H, s), 3.07 (1H, m), 3.48 (2H, d), 4.84 (1H, s), 5.07 (1H, dd), 5.09 (1H, dd), 6 (1H, m), 6.81 (1H, d), 7.01 (1H, d); $^{13}$C NMR (125 MHz, CDCl$_3$) 15.8, 24.0, 29.3, 30.1, 115.8, 117.3, 121.1, 122.1, 128.9, 136.6, 146.1, 152.4 ppm.

Para Allyl Carvacrol (2b):

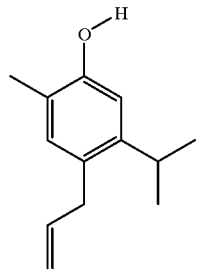

MS: M$^+$=190; $^1$H NMR (CDCl$_3$, 500 MHz) δ 1.18 (6H, d), 2.19 (3H, s), 3.05 (1H, m), 3.33 (2H, d), 4.54 (1H, s), 4.99 (1H, dd), 5.02 (1H, dd), 5.94 (1H, m), 6.69 (1H, s), 6.88 (1H, s); $^{13}$C NMR (125 MHz, CDCl$_3$) 15.2, 23.9, 28.7, 36.3, 111.9, 115.1, 120.7, 128.8, 132.3, 138.3, 146.1, 152.6 ppm.

EXAMPLES 3a AND 3b

Ortho and Para Propyl Thymol:

To a flask containing 5% Pd/C (1 g), a solution of allyl thymol (20 g, 105 mmole) in solvent (300 ml, 10% ethanol in ethyl acetate) was added. The reaction mixture was treated with hydrogen (40 psi) in a Parr hydrogenation apparatus for 3 hours. The mixture was filtered through silica gel and the filtrate was concentrated via rotary evaporation. The mixture was distilled under vacuum (79–80° C. @ 0.6 mm Hg) to afford a colorless oil (19.6 g, 98%) consisting of ortho and para isomers (ortho:para=24:1 by GC). If desired, the isomers can be separated via silica gel column chromatography (10% ethyl ether in hexane) to provide ortho propyl thymol (3a) and para propyl thymol (3b).

Ortho Propyl Thymol (3a):

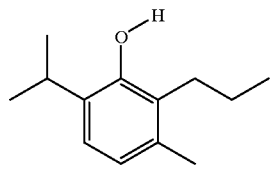

MS: M⁺=192; ¹H NMR (CDCl₃, 500 MHz) δ 1.02 (3H, t), 1.25 (6H, d), 1.56 (2H, m), 2.27 (3H, s), 2.58 (2H, t), 3.10 (1H, m), 4.70 (1H, s), 6.73 (1H, dd), 6.94 (1H, dd); ¹³C NMR (125 MHz, CDCl₃) 14.6, 19.5, 22.5, 22.9, 27.1, 29.0, 122.5, 123.2, 126.7, 131.4, 134.8, 150.9 ppm.

Para Propyl Thymol (3b):

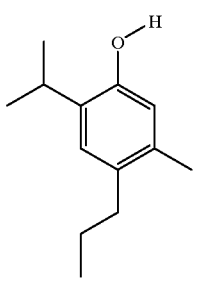

MS: M⁺=192; ¹H NMR (CDCl₃, 500 MHz) δ 0.98 (3H, t), 1.25 (6H, d), 1.56 (2H, m), 2.20 (3H, s), 2.50 (2H, t), 3.15 (1H, m), 4.54 (1H, s), 6.55 (1H, s), 6.94 (1H, s); ¹³C NMR (125 MHz, CDCl₃) 14.2, 18.8, 22.8, 23.9, 26.9, 35.0, 117.1, 127.1, 131.5, 133.3, 134.2, 150.5 ppm.

EXAMPLES 4a AND 4b

Ortho and Para Propyl Carvacrol:

These materials were prepared as described in Example 3. From allyl carvacrol (20.0 g, 105 mmole) was obtained a colorless oil (19.7 g, 98%, 82–83° C. @ 0.6 mm Hg) consisting of ortho and para isomers (ortho:para=9:1 by GC). If desired, the isomers can be separated via silica gel column chromatography (10% ethyl ether in hexane) to provide ortho propyl carvacrol (4a) and para propyl carvacrol (4b).

Ortho Propyl Carvacrol (4a):

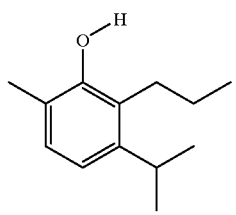

MS: M⁺=192; ¹H NMR (CDCl₃, 500 MHz) δ 1.03 (2H, t), 1.21 (6H, d), 1.55 (2H, m), 2.21 (3H, s), 2.63 (2H, t), 3.12 (1H, m), 4.59 (1H, s), 6.79 (1H, d), 6.96 (1H, d); ¹³C NMR (125 MHz, CDCl₃) 14.6, 15.9, 23.6, 24.3, 27.9, 28.9, 117.3, 119.9, 125.6, 128.2, 146.2, 151.7 ppm.

Para Propyl Carvacrol (4b):

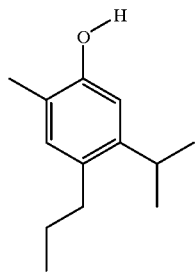

MS: M⁺=192; ¹H NMR (CDCl₃, 500 MHz) δ 0.99 (3H, t), 1.20 (6H, d), 1.57 (2H, m), 2.21 (3H, s), 2.52 (2H, t), 3.11 (1H, m), 4.63 (1H, s), 6.69 (1H, s), 6.89 (1H, s); ¹³C NMR (125 MHz, CDCl₃) 14.3, 15.3, 24.2, 25.2, 28.6, 34.3, 111.9, 120.6, 131.8, 132.1, 145.8, 152.1 ppm.

EXAMPLE 5

Ortho Allyl Para tert-Butyl Phenol

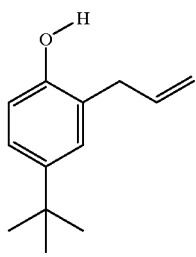

This material was prepared as described in Example 1. From allyl para tert-butyl phenyl ether (105.0 g, 553 mmole) was obtained ortho allyl para tert-butyl phenol as a colorless oil (84.0 g, 80%, 100–105° C. @ 0.75 mm Hg).

MS: M⁺=190 ¹H NMR (CDCl₃, 500 MHz): δ 1.97 (9H, s), 3.40 (2H, d), 5.16 (2H, d), 6.04 (1H, m), 6.74 (1H, d), 7.10 (1H,s), 7.15 (1H, d); ¹³C NMR (CDCl₃, 125 MHz): 32, 36, 115, 116, 125, 127, 137, 144, 152 ppm.

EXAMPLE 6

Ortho Propyl Para tert-Butyl Phenol:

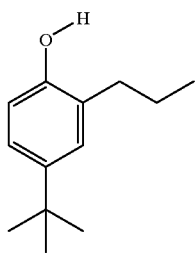

This material is prepared as described in Example 3. From ortho allyl para tert-butyl phenol (40.0 g, 211 mmole) is obtained ortho propyl para tert-butyl phenol as a colorless oil (40.4 g, 100%, 144–145° C. @ 0.45 mm Hg).

MS: M+=192; ¹H NMR (CDCl₃, 500 MHz): δ 0.95 (3H, t), 1.27 (9H, s), 1.65 (2H, m), 2.55 (2H, t), 4.50 (1H, s), 6.69 (1H, d), 7.08 (1H, d), 7.11 (1H, d); ¹³C NMR (CDCl₃, 125 MHz): 14, 23, 32, 33, 114, 124, 127, 128, 143, 151 ppm.

The odor qualities of the materials were evaluated by an expert panel of perfumers (approximately 25 individuals). Samples of the materials to be evaluated were applied, either neat or in solution, to chemically pure perfume blotters and were assessed for standard odor characteristics. The results of the assessments are shown below.

| Example | Odor Qualities |
| --- | --- |
| Example 1 (1a + 1b) | thyme-like, leathery, herbal, spicy |
| Example 2 (2a + 2b) | woody, herbaceous, mushroom like |
| Example 3 (3a + 3b) | woody, spicy, leathery, herbaceous |
| Example 4 (4a + 4b) | woody, leathery, spicy |

-continued

| Example | Odor Qualities |
| --- | --- |
| Example 5 | leathery, woody, herbal |
| Example 6 | woody, rubbery, floral |

The flavor qualities of the materials were evaluated by an expert panel of flavorists (approximately 10 individuals). Solutions (8 ppm in water) of the materials to be evaluated were assessed for standard flavor characteristics via a "swish and spit" method. The results of these assessments are shown below.

| Example | Flavor Qualities |
| --- | --- |
| Example 1 (1a + 1b) | oily, slightly sweet vanillin, phenolic |
| Example 2 (2a + 2b) | dried herbal, slightly spicy, slightly phenolic |
| Example 3 (3a + 3b) | medicinal, bitter, slightly sweet vanillin, phenolic |
| Example 4 (4a + 4b) | medicinal, bitter, slightly spicy, slightly phenolic |

The anti-microbial activity of Examples 1–6 were evaluated. All materials tested showed significant activity against gram positive bacteria (see Table 1 below). Whether tested alone or in combination, these materials exhibited significantly greater activity against gram positive microorganisms than the thymol and carvacrol standards; the minimum inhibition concentration (MIC) for Examples 1–6 were lower than those of thymol and carvacrol.

The anti-microbial activity of a dilute solution of the flavor and fragrance compositions of the present invention is measured as the log of the reduction in bacterial number at 5 and 30 minutes. This measurement is labeled as "log reduction @ 5 min" and "log reduction @ 30 min" in Tables 4 and 6, respectively.

TABLE 1

Anti-Microbial Activity of Examples 1–6 (MIC in μg/mL)

| Organism | S. a. | S. e. | S. m. | P. acnes | C. m. | C. x. | A. neasl |
| --- | --- | --- | --- | --- | --- | --- | --- |
| strain: | 6535 | 1228 | 25175 | 6919 | 23348 | 373 | 19039 |
| type: | gram+ | gram+ | gram+ | gram+ | gram+ | gram+ | gram+ |
| Example: | | | | | | | |
| 1(1a + 1b) | 62.5 | 62.5 | 62.5 | 62.5 | 62.5 | 62.5 | 62.5 |
| 1a | 62.5 | 62.5 | 62.5 | 62.5 | 62.5 | 62.5 | 62.5 |
| 1b | 62.5 | 62.5 | 31.25 | 31.25 | 62.5 | 62.5 | 62.5 |
| 2(2a + 2b) | 62.5 | 125 | 62.5 | 62.5 | 125 | 62.5 | |
| 2a | 62.5 | 62.5 | 62.5 | 31.25 | 62.5 | 62.5 | 62.5 |
| 2b | 62.5 | 62.5 | 62.5 | 62.5 | 62.5 | 62.5 | |
| 3(3a + 3b) | 62.5 | 62.5 | 31.25 | 31.25 | 31.25 | 62.5 | 62.5 |
| 3a | 62.5 | 62.5 | 31.25 | 31.25 | 62.5 | 62.5 | 62.5 |
| 3b | 31.25 | 31.25 | 31.25 | 31.25 | 31.25 | 31.25 | 31.25 |
| 4(4a + 4b) | 31.25 | 31.25 | 31.25 | 31.25 | 31.25 | 31.25 | 31.25 |
| 4a | 125 | 31.25 | 31.25 | 31.25 | 31.25 | 31.25 | 31.25 |
| 4b | ≤15.6 | 31.25 | ≤15.6 | ≤15.6 | ≤15.6 | ≤15.6 | ≤15.6 |
| 5 | 31.25 | 31.25 | | 15.6 | 31.25 | 31.25 | |
| 6 | 15.6 | 15.6 | | 7.8 | 15.6 | 15.6 | |
| Thymol | 250 | 250 | 250 | 125 | 125 | 250 | 125 |
| carvacrol | 125 | 125 | 125 | 125 | 125 | 125 | 125 |

Key to abbreviations:
S. a. Staphylococcus aureus
S. e. Staphylococcus epidermidis
S. m. Steptococcus mutans
P. acnes Propionibacterium acnes
C. m. Corynebacterium minutissimum
C. x. Corynebacterium xerosis
A. neasl. Actinomyces neaslundii In addition, the activity of Examples 1–6 against fungi was only slightly better than that of thymol and carvacrol (see Table 2 below). In contrast to their activity against gram positive bacteria and fungi, Examples 1–6 showed only slight activity against the gram negative organisms E. coli and P. aeruginosa (see Table 2 below).

TABLE 2

Anti-Microbial Activity of Examples 1–6 (MIC in μg/mL)

| Organism: | E. c. | P. aerug. | C. a. | A. niger |
| --- | --- | --- | --- | --- |
| strain: | 11229 | 15442 | 10231 | 16404 |
| type: | gram - | gram - | fungi | fungi |

TABLE 2-continued

Anti-Microbial Activity of Examples 1–6 (MIC in µg/mL)

| Example | | | | |
|---|---|---|---|---|
| 1 (1a + 1b) | >1000 | >1000 | 125 | 125 |
| 1a | >1000 | >1000 | 125 | 125 |
| 1b | >1000 | >1000 | 125 | 125 |
| 2 (2a + 2b) | >1000 | >1000 | 125 | 125 |
| 2a | >1000 | >1000 | 125 | 125 |
| 2b | | | 125 | 125 |
| 3 (3a + 3b) | >1000 | >1000 | 125 | 125 |
| 3a | >1000 | >1000 | 125 | 125 |
| 3b | >1000 | >1000 | 62.5 | 125 |
| 4 (4a + 4b) | >1000 | >1000 | 125 | 125 |
| 4a | >1000 | >1000 | 62.5 | 125 |
| 4b | >1000 | >1000 | 62.5 | 62.5 |
| 5 | >500 | | | |
| 6 | >500 | | | |
| thymol | 250 | >1000 | 250 | 125 |
| carvacrol | 500 | >1000 | 250 | 250 |

Key to abbreviations:
E. c. Escherichia coli
P. aerug. Pseudomonas aeruginosa
C. a. Candida albicans
A. niger Aspergillus niger Embodiment 1 (E1)—Fragrance Formulation

| Name | Formula Parts | Weight % |
|---|---|---|
| ortho propyl carvacrol | 200.0 | 20.0 |
| clove leaf oil | 20.0 | 2.00 |
| orange oil california | 400.0 | 40.00 |
| d-limonene | 200.0 | 20.00 |
| mandarin accord 005A | 122.5 | 12.25 |
| phellandrene, alpha | 50.0 | 5.00 |
| linalool, syn | 7.5 | 0.75 |
| Total | 1000.0 | 100.00 |

The fragrance compositions of the invention may, if desired, contain a carrier or vehicle. Such carriers include liquids such as a non-toxic alcohol, a non-toxic glycol, or the like. An example of a non-toxic alcohol is ethyl alcohol. An example of a non-toxic glycol is 1,2-propylene glycol. Alternatively, the carrier can be an absorbent solid such as a gum, e.g., gum arabic, xanthan gum. The amount of the carrier will vary depending upon the particular carrier employed and its intended use, as will be readily apparent to those skilled in the art.

Embodiment 2 (E2)—Flavor Formulation

| Name | Formula Parts | Weight % |
|---|---|---|
| ortho propyl carvacrol | 5.0 | 5.00 |
| mint flavor* | 15.0 | 65.00 |
| methyl salicylate | 5.0 | 5.00 |
| menthol | 5.0 | 5.00 |
| peppermint oil | 15.0 | 15.00 |
| star anise oil | 2.5 | 2.50 |
| cinnamic aldehyde | 2.5 | 2.50 |
| Total | 100.00 | 100.00 |

*manufactured by Takasago International Corp., Tokyo, Japan

The flavor compositions of the invention may, if desired, contain a carrier or vehicle. Such carriers include liquids such as water. The amount of the carrier will vary depending upon the particular carrier employed and the intended use of the flavor composition, and will be readily apparent to those skilled in the art.

Embodiment 3 (E3)—Antimicrobial Activity of E1 Fragrance Composition

As used herein, the term "sanitizing" is understood by those in the art to mean a reduction in viable microbial number (measured in colony forming units, or cfu) after exposure to the agent on an order of 3.0 log cfu/ml or higher. The term "disinfecting" is understood by those in the art to mean a reduction in viable microbial number after exposure to the agent on an order of 5.0 log cfu/ml or higher. The term "antimicrobial" as used herein refers to either or both inhibiting growth and reducing the viable microbial number.

Antimicrobial activity was evaluated to determine minimal inhibitory concentration ("MIC") and Minimal Bactericidal Concentration ("MBC"). The specific biological testing protocol is published R. Kang et al., "J. Agric. Food Chem.," vol. 40 pp. 2328–2330 (1994), the entirety of which is herein incorporated by reference. Results of the test are summarized in Tables 3 and 4 below.

TABLE 3

Antimicrobial Activity of Fragrance Composition E1

| Bacteria Strain | MIC (wt %) | MBC (wt %) |
|---|---|---|
| S. aureus 6538 | 0.0156 | 0.0312 |
| E. coli 11229 | >0.25 | — |

The results show that to achieve MIC against S. aureus, a gram positive bacteria, only 156 ppm of the fragrance composition is required. To achieve MBC for that same bacteria, only 312 ppm is required. When tested against E. coli, a common gram negative bacteria, greater than 2,500 ppm was required to achieve MIC.

TABLE 4

Antimicrobial Activity of a 0.25% Solution of Fragrance Composition E1

| Bacteria Strain | Log Reduction at 5 minutes | Log Reduction at 30 minutes |
|---|---|---|
| S. aureus 6538 | 1 | 1.5 |
| E. coli 11229 | 0.5 | 0.6 |

The results show that when a 0.25% concentration of the fragrance composition of Embodiment 3 is used against S. aureus, an approximate tenfold reduction occurs within 5 minutes. An approximate 30 fold reduction occurs within 30 minutes of exposure. When the same concentration of the fragrance composition of Embodiment 3 is used against E. coli, an approximate three fold reduction occurred within 5 minutes and an approximate four fold reduction occurred within 30 minutes.

Embodiment 4 (E4)—Antimicrobial Activity of E2 Flavor Composition

TABLE 5

Antimicrobial Activity of Flavor Composition E2

| Antimicrobial Activity | MIC (wt %) | MBC (wt %) |
|---|---|---|
| S. aureus 6538 | 0.0156 | 0.0312 |
| E. coli 11229 | 0.25 | >0.25 |

The results show that to achieve MIC against S. aureus, only 156 ppm of the flavor composition is required. To achieve MBC for that same bacteria, only 312 ppm is required. When tested against *E. coli*, 2,500 ppm was required to achieve MIC and greater than 2,500 ppm was required to achieve MBC.

TABLE 6

Antimicrobial Activity of a 0.25% Solution of Flavor Composition E2

| Bacteria Strain | Log Reduction at 5 minutes | Log Reduction at 30 minutes |
|---|---|---|
| *S. aureus* 6538 | 0.8 | 1.2 |
| *E. coli* 11229 | 3.3 | >4 |

The results show that when a 0.25% concentration of the flavor composition of Embodiment 2 is used against *S. aureus*, an approximate sixfold reduction occurs within 5 minutes. An approximate 15 fold reduction occurs within 30 minutes of exposure. When the same concentration of the flavor composition of Embodiment 2 is used against *E. coli*, an approximate 2,000 fold reduction occurred within 5 minutes and a reduction of more than ten thousand fold occurred within 30 minutes.

Embodiment 5 (E5)—Cleanser Using E1 Fragrance Composition

A detergent was made using the fragrance composition of Embodiment 1 (E1). The Embodiment 5 was made by admixture of the fragrance composition E1 into a cleanser. The fragrance composition is suitable for use in cleaning agents, hair sprays, soaps and related products by admixture in suitable quantities selected based on the need of the individual product. Alternatively, other methods that are well known in the art may be used to make these products with the fragrance composition.

| Name | Weight % |
|---|---|
| sodium xylene solfonate | 12.5 |
| Triton C-100 ® | 5.0 |
| Sodium dodecylbenzenesulfonate | 3.5 |
| Sodium sesquicarbonate | 2.5 |
| Sodium citrate dihydrate | 2.5 |
| Neodol 25-3 ® | 1.0 |
| Fragrance (Embodiment 1) | 1.0 |
| Deionized water | 72.0 |
| Total | 100.0 |

Embodiment 6 (E6)—Mouth Wash Using E2 Flavor Composition

A mouth wash was made using the flavor composition of Embodiment 2 (E2). The Embodiment 6 was made by admixture of the flavor composition E2 into a mouthwash. The flavor composition is suitable for use in toothpastes, cough drops, nebulizers, inhalants and related products by admixture in suitable quantities that are selected based on the need of the individual product. Alternatively, other methods that are well known in the art may be used to make these products with the flavor composition.

| Name | Weight % |
|---|---|
| Ethyl alcohol | 10.0 |
| Sodium saccharine USP | 2.5 |

-continued

| Name | Weight % |
|---|---|
| Tween ® 60 | 0.4 |
| Sodium benzoate | 0.2 |
| Citric acid | 0.1 |
| Green color (0.1 wt. % FD&C green in $H_2O$) | 0.1 |
| Flavor (Embodiment E2) | 0.2 |
| Distilled water | 86.5 |
| Total: | 100.0 |

Having described preferred embodiments of the invention, it is to be understood that the invention is not limited to those precise embodiments, and that various changes and modifications may be effected therein by one skilled in the art without departing from the scope or spirit of the invention as defined in the appended claims.

What is claimed is:

1. A method of using a compound of the following formula (I):

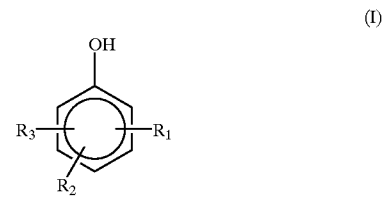

wherein $R_1$ is one of a propyl or a 2-propenyl group, $R_2$ is one of a hydrogen atom and a $C_1$–$C_5$ straight-chained or branched alkyl group, and $R_3$ is a $C_3$–$C_5$ straight-chained or branched alkyl group, said compound having exactly one $R_1$, exactly one $R_2$, and from one to three $R_3$, as at least one of a fragrance and a flavor, comprising forming a composition containing an effective amount of said compound with a suitable carrier.

2. A method according to claim 1, wherein said compound is para allyl thymol.

3. A method according to claim 1, wherein said compound is ortho allyl cavacrol.

4. A method according to claim 1, wherein said compound is para allyl cavacrol.

5. A method according to claim 1, wherein:
said composition is a fragrance composition;
said suitable carrier includes at least one of a non-toxic alcohol, a non-toxic glycol, and an absorbent solid; and
said effective amount is from about 0.05 weight percent to about 20.00 weight percent.

6. A method according to claim 1, wherein:
said composition is a flavor composition;
said suitable carrier is water; and
said effective amount is from about 0.05 weight percent to about 5.00 weight percent.

7. A method according to claim 1, further comprising admixing said composition with appropriate adjunct ingredients to form a product, whereby said product is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, hair care product, mouthwash, toothpaste, and a fabric softener.

8. A fragrance composition, comprising
a substituted phenol having the following formula (I):

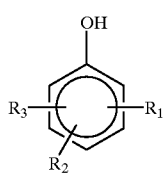

(I)

wherein $R_1$ is one of a propyl or a 2-propenyl group, $R_2$ is one of a hydrogen atom and a $C_1$–$C_5$ straight-chained or branched alkyl group, and $R_3$ is a $C_3$–$C_5$ straight-chained or branched alkyl group, said compound having exactly one $R_1$, exactly one $R_2$, and from one to three $R_3$; and a suitable carrier.

9. A fragrance composition according to claim 8, wherein the hydroxyl group and $R_1$ are in a 1,2 substitution relationship.

10. A fragrance composition according to claim 8, wherein the hydroxyl group and $R_1$ are in a 1,4 substitution relationship.

11. A fragrance composition according to claim 8, wherein said substituted phenol compound is at least one of the group consisting of: ortho allyl thymol, para allyl thymol, ortho allyl carvacrol, para allyl carvacrol, ortho propyl thymol, para propyl thymol, ortho propyl carvacrol, para propyl carvacrol, ortho allyl para tert-butyl phenol, and ortho propyl para tert-butyl phenol.

12. A fragrance composition according to claim 8, wherein said substituted phenol compound is at least one of ortho allyl thymol and para allyl thymol.

13. A fragrance composition according to claim 8, wherein said substituted phenol compound is at least one of ortho allyl carvacrol and para allyl carvacrol.

14. A fragrance composition according to claim 8, wherein said substituted phenol compound is at least one of ortho propyl thymol and para propyl thymol.

15. A fragrance composition according to claim 8, wherein said substituted phenol compound is at least one of ortho propyl carvacrol and para propyl carvacrol.

16. A fragrance composition according to claim 8, wherein said substituted phenol compound is ortho propyl para tert-butyl phenol.

17. A fragrance composition according to claim 8, wherein said substituted phenol compound is ortho allyl para tert-butyl phenol.

18. A fragrance composition according to claim 8, wherein said fragrance composition possesses antimicrobial activity against at least one of the group consisting of gram positive bacteria and fungi.

19. A fragrance composition according to claim 8, further comprising:
an antimicrobial agent effective against gram negative bacteria wherein said fragrance composition is effective to impart broad spectrum antimicrobial activity.

20. A fragrance composition according to claim 8, further comprising appropriate adjunct ingredients to form a product, whereby said product is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, hair care products, and a fabric softener.

21. A flavor composition comprising:
a substituted phenol having the following formula (I):

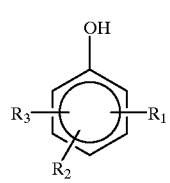

(I)

wherein $R_1$ is one of a propyl or a 2-propenyl group, $R_2$ is one of a hydrogen atom and a $C_1$–$C_5$ straight-chained or branched alkyl group, and $R_3$ is a $C_3$–$C_5$ straight-chained or branched alkyl group, said compound having exactly one $R_1$, exactly one $R_2$, and from one to three $R_3$; and a suitable carrier.

22. A flavor composition according to claim 21, wherein the hydroxyl group and $R_1$ are in a 1,2 substitution relationship.

23. A flavor composition according to claim 21, wherein the hydroxyl group and $R_1$ are in a 1,4 substitution relationship.

24. A flavor composition according to claim 21, wherein said substituted phenol compound is at least one of the group consisting of: ortho allyl thymol, para allyl thymol, ortho allyl carvacrol, para allyl carvacrol, ortho propyl thymol, para propyl thymol, ortho propyl carvacrol, para propyl carvacrol, ortho allyl para tert-butyl phenol, and ortho propyl para tert-butyl phenol.

25. A flavor composition according to claim 21, wherein said substituted phenol compound is at least one of ortho allyl thymol and para allyl thymol.

26. A flavor composition according to claim 21, wherein said substituted phenol compound is at least one of ortho allyl carvacrol and para allyl carvacrol.

27. A flavor composition according to claim 21, wherein said substituted phenol compound is at least one of ortho propyl thymol and para propyl thymol.

28. A flavor composition according to claim 21, wherein said substituted phenol compound is at least one of ortho propyl carvacrol and para propyl carvacrol.

29. A flavor composition according to claim 21, wherein said substituted phenol compound is ortho propyl para tert-butyl phenol.

30. A flavor composition according to claim 21, wherein said substituted phenol compound is ortho allyl para tert-butyl phenol.

31. A flavor composition according to claim 21, wherein said flavor composition possesses antimicrobial activity against at least one of the group consisting of gram positive bacteria and fungi.

32. A flavor composition according to claim 21, further comprising:
a non-toxic antimicrobial agent effective against gram negative bacteria; said flavor composition being in an amount effective to impart broad spectrum antimicrobial activity.

33. A flavor composition according to claim 21, further comprising at least one additive to form a product, whereby said product is effective to act as at least one of a tooth paste, a mouth wash, a cough drop, a nebulizer and an inhalant.

* * * * *